US007711499B2

(12) United States Patent
Junker et al.

(10) Patent No.: US 7,711,499 B2
(45) Date of Patent: May 4, 2010

(54) EDDY CURRENT DATA INTERPOLATION/EXTRAPOLATION

(75) Inventors: Warren R. Junker, Monroeville, PA (US); Thomas W. Nenno, Murrysville, PA (US); Daniel J. Yaklich, Export, PA (US); Ronald J. Pocratsky, Acme, PA (US)

(73) Assignee: Westinghouse Electric Co LLC, Cranberry Township, PA (US)

( * ) Notice: Subject to any disclaimer, the term of this patent is extended or adjusted under 35 U.S.C. 154(b) by 390 days.

(21) Appl. No.: 11/954,043

(22) Filed: Dec. 11, 2007

(65) Prior Publication Data

US 2009/0150093 A1    Jun. 11, 2009

(51) Int. Cl.
*G01B 5/28* (2006.01)
*G06F 19/00* (2006.01)

(52) U.S. Cl. .................... 702/38; 324/237; 324/240; 702/75; 702/85

(58) Field of Classification Search ............... 702/33, 702/35, 38, 65, 75, 76, 85, 106, 182–186, 702/189; 324/202, 225, 237, 238, 240, 242; 73/601
See application file for complete search history.

(56) References Cited

U.S. PATENT DOCUMENTS

| | | | |
|---|---|---|---|
| 6,823,269 B2 | 11/2004 | Junker et al. | |
| 6,975,108 B2 * | 12/2005 | Bilik et al. | 324/237 |
| 7,355,395 B2 * | 4/2008 | Redko et al. | 324/240 |
| 2004/0257072 A1 * | 12/2004 | Samson | 324/242 |

* cited by examiner

*Primary Examiner*—John H Le

(57) ABSTRACT

A method of synthesizing nondestructive examination data of a component that combines data sets acquired at least two different frequencies. At least one of the data sets is interpolated or extrapolated to the equivalent of data acquired at one of the other frequencies employing a third, reference set of eddy current inspection data that is acquired at each of the inspection frequencies being combined.

12 Claims, 4 Drawing Sheets

EDDY CURRENT DATA INTERPOLATION/EXTRAPOLATION

BACKGROUND OF THE INVENTION

1. Field of the Invention

The invention pertains generally to eddy current data obtained from non-destructive examination of a component and more particularly, to a method of combining eddy current data obtained at two different scanning frequencies.

2. Description of the Prior Art

Nondestructive examination of components is carried out in a number of fields and is particularly important in the periodic inspection of steam generator tubing that form part of the primary circuit of a pressurized water reactor nuclear steam supply system. The integrity of the steam generator tubing in the primary circuit of a pressurized water nuclear reactor steam supply system is essential to assure that radioactive coolant from the reactor does not contaminate the secondary side circuit in which it is in heat transfer relationship to create steam to drive a turbine which in turn drives a generator to create electricity. A hot leg of the nuclear reactor primary coolant circuit is connected to one side of a hemispherical plenum on the underside of the steam generator. The hemispherical plenum is divided into two substantially equal parts and bounded on its upper side by a tube sheet. Heat exchanger tubes extend from one side of the hemispherical plenum through the tube sheet into the secondary side in a U-shaped design that terminates through the tube sheet to the other side of the hemispherical plenum. The other side of the hemispherical plenum is connected to a cold leg of the nuclear reactor primary coolant circuit. There are hundreds of tubes within the steam generator communicating between the hot side and the cold side of the plenum. To ensure the integrity of the tubes, periodically, during reactor outages, the plenum is accessed through manways and the tubes inspected. Eddy current probes are inserted into the tubes and the tube position and data read by the eddy current detectors are recorded to identify any flaws that may have developed in the tubes during the preceding service period between inspections. The eddy current data takes the form of signal patterns, which require a great deal of experience to interpret to identify the existence, type and extent of any flaws that may be present in the tubing. If flaws are detected that exceed a given criteria, the corresponding tubing is plugged and thus taken out of service to reduce the likelihood of failure during the forthcoming reactor operating cycle.

Obtaining eddy current data representative of the various kinds of flaws that are likely to be encountered under field conditions, among a background of scattering data and other noise encountered in the field, to train data analysts and test inspection techniques, is extremely difficult and expensive. However, such training is essential to being able to properly interpret eddy current data. Similarly, the testing of inspection techniques is necessary to understand the probability of detecting different types of flaws and the affect the sizing of a flaw has on the various discontinuity responses.

Accordingly, a need exists to acquire eddy current data representative of the detection of a number of different flaws that is suitable for training and qualifying analysts and testing inspection techniques. Desirably, such data should have substantially the same background, scatter and other noise as is encountered in the field.

U.S. Pat. No. 6,823,269 addresses this need by teaching a method for synthesizing eddy current data for this purpose. The steps of the method involve creating a specimen that simulates the component undergoing nondestructive examination with preselected flaws of interest. The specimen is then monitored by an eddy current probe to create a set of eddy current data representative of the flaws detected in the specimen. At least some of the eddy current data collected at a field site is combined with at least some of the eddy current data collected from the specimen to establish a combined data train that reflects the eddy current response to the selected flaws in a background representative of data collected at the field site. Preferably, the eddy current probes used to collect data at the field site and at the specimen are the same type and are operated at the same inspection frequencies and data sampling rates. Furthermore, the patent teaches that it is desirable that the field and specimen data sets are calibrated separately to substantially the same standard so that the signal level and orientation for a given flaw correspond. However, the patent reference recognizes in the real world there will be differences in monitoring conditions between the field data set and the data set obtained from the specimen and states that if there are differences in the inspection conditions, mathematical models can be used to interpolate one or the other of the responses if coil size or inspection frequencies are not identical.

Initially, simple linear combinations of the inspection results from two frequencies were used in an attempt to infer the response at an intermediate frequency. While this produces a result that approximates the desired response it was found that it lacked many of the subtleties present in the original data. It was determined that the shortcoming of the approach was a consequence of the frequency dependent field spread associated with the eddy current coil. This leads to a response being in the lower frequency data at locations where there was none at the higher frequency. A simple combination of the two responses is satisfactory where the two responses overlap but is inadequate where they do not.

Accordingly, a new method is desired that would enable the data union method to be employed with two or more data sets obtained at different frequencies.

Furthermore, such a method is desired that would enable the combination of different data sets obtained at different frequencies without the loss of any of the information in the original data sets.

SUMMARY OF THE INVENTION

These and other objects are achieved by the method of this invention for interpolating or extrapolating eddy current inspection data at a desired frequency. The method acquires a first set of eddy current inspection data at a first frequency, a second set of eddy current inspection data at a second frequency and a reference set of eddy current inspection data at the first frequency, the second frequency and at the desired frequency. The method then infers the eddy current inspection data at the desired frequency based upon the first set, the second set and the reference set of eddy current inspection data. In most instances, the desired frequency will be one or the other of the first frequency or the second frequency. All three or more data sets should be obtained from the same type of probe and under substantially similar inspection conditions. The remaining two or more data sets should be rotated and scaled to the data set obtained at the desired frequency before interpolation or extrapolation. Desirably, the reference data set should include a number of responses to different discontinuities and structures that are likely to be encountered in a field inspection.

BRIEF DESCRIPTION OF THE DRAWINGS

Further understanding of the invention can be gained from the following description of the preferred embodiments when read in conjunction with the accompanying drawings in which.

DESCRIPTION OF THE PREFERRED EMBODIMENTS

Figure 1:
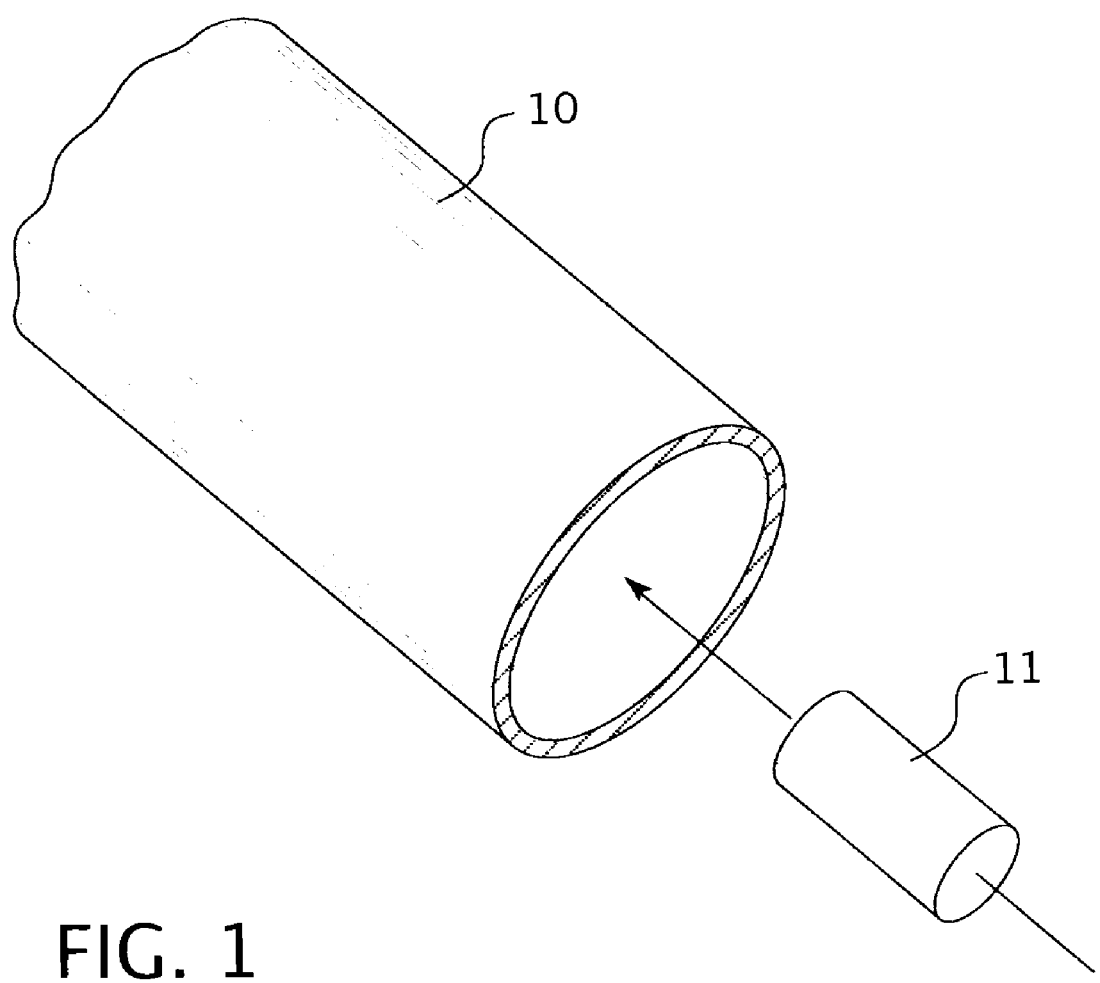
FIG. 1 is a perspective view of a portion of a steam generator tube in which an eddy current probe is about to be inserted.

In the inspection of steam generator tubes (10) by nondestructive eddy current probes (11) (as figuratively shown in FIG. 1) eddy current data is routinely acquired for a number of different inspection frequencies and from a number of different eddy current coils. In modern instrumentation all timing and data acquisition are conducted digitally so that all eddy current data are assumed to be in digital format, although the described process could be accomplished in analog also. At each inspection interval data are acquired (often referred to as a time slice or just slice) for each of the coils at each of the frequencies in a prescribed order. The data are then stored in the prescribed order in an array. At the next interval the process is repeated such that, typically, each interval of data corresponds to some relative motion of the coils over the part under inspection. For coils pulled though a tube (10), e.g., a bobbin coil (11), the response for each coil and frequency are two one dimensional arrays with adjacent elements, corresponding to different coil positions along the axis of the tube. For coils that raster over a surface or are rotated inside a tube the resulting data are also in a time sequence, however, the response resulting from a particular location on the part being tested now occurs during a sequence of slices separated by multiple intervals determined by the scanning pattern.

The algorithm of this invention incorporates a set of coefficients that are multiplied by the responses obtained for the desired coil at the measurement frequencies and for inspection intervals associated with the location of interest within the overall data set. For data obtained from a bobbin coil this corresponds to intervals adjacent to one of interest. For raster data the process includes data from both adjacent intervals and also those intervals that are adjacent spatially within the coil motion. For simplicity what follows is a description of the algorithm as applied to bobbin coil data.

To begin, assume that there are two sets of inspection data that were acquired with similar probes and similar inspection conditions such that the only difference is that the set of inspection frequencies are different. Further, both data sets have been appropriately rotated and scaled to allow for their data to be appropriately combined. Again, for simplicity, it is assumed that there is only one inspection frequency that is different between the two data sets i.e. Set A uses frequencies $f_1$, $f_a$, and $f_3$ and Set B uses frequencies $f_1$, $f_b$ and $f_3$ where $f_1 > f_a$ and $f_b > f_3$. The desire is to combine data Set A with data Set B requiring that data at the response at $f_b$ be interpolated from $f_1$, $f_a$ and $f_3$. For each data interval (t) the relationship between the measurement at $f_b$ and the measurement at $f_1$, $f_a$ and $f_3$ can be written:

$$C^*(A) = (B)$$

Where C is the matrix of coefficients $C_{11}\ C_{12}\ C_{13}\ \ldots\ C_{1m}$ $C_{21} C_{22} C_{23}\ \ldots\ C_{2m}$ and A is a vector of x(f) and y(f) components at each of the frequencies $f_1$, $f_a$ and $f_3$ for the various data intervals t−n*d, t−(n−)*d . . . t . . . t+(n−1)*d, t+n*d where n is the number of slices to include before and after t and d is the distance between slices and m is the largest dimension of the coefficient matrix and is related to n and the number of frequencies used in the interpolation/extrapolation.

$$A = (x(f_1)_{t-n^*d} \ldots x(f_1)_t \ldots x(f_1)_{t+n^*d}, y(f_1)_{t-n^*d} \ldots y(f_1)_t \ldots y(f_1)_{t+n*d}, x(f_a)_{t-n^*d} \ldots x(f_a)_{t+n*d}, y(f_3)_{t-n^*d} \ldots y(f_3)_{t+n^*d})^T$$

So that m=2*number of frequencies*(2n+1)=6*(2*n+1)

And $B = (x(f_b)_t, y(f_b)_t)^T$

After B is calculated for each data interval the entire set is inserted in place of the portion of data Set A that contains the inspection data obtained at inspection frequency $f_a$. The resulting data set (Set A') can then be combined with data Set B as per the Data Union process described in U.S. Pat. No. 6,823,269.

To implement this procedure, however, the coefficient matrix must be calculated. This requires that a third set of data (Set R) exists or is created that includes inspection results from all of the inspection frequencies that are to be included in the interpolation/extrapolation process. For the example this means that the data Set R contain data obtained at the inspection frequencies $f_1$, $f_a$, $f_b$ and $f_3$. Again data Set R must be acquired in a manner consistent with data Sets A and B and rotated and scaled appropriately. Within Set R responses for a number of discontinuities and structures must be present, so that it is most appropriately the data from a calibration tube. The process to calculate the coefficient matrix C is as follows.

Vectors A and B are constructed from the appropriate subset of data Set R. For each interval the following is constructed $$\lambda = (C^*(A) - B)$$

C is the set of coefficients that minimizes $(\lambda)^2$ for the data intervals containing the responses of interest. Once matrix C is calculated it can be utilized to interpolate inspection frequencies for any data set that has been obtained in a fashion similar to Set R. This includes data obtained from different tubing sizes provided that the inspection frequencies have been appropriately scaled.

Figure 2:
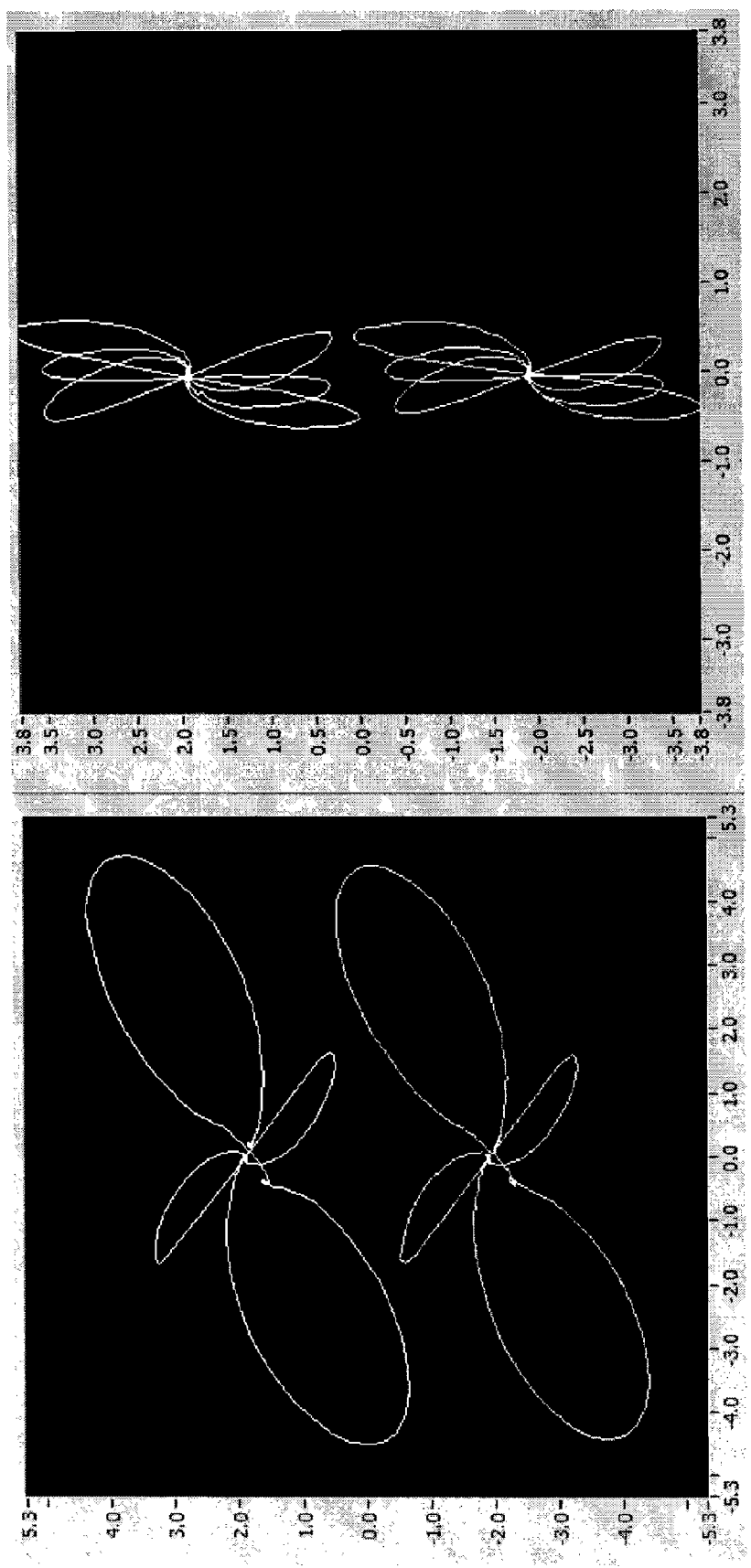
FIG. 2 is a computer screen image of a comparison of 200 kHz response of the calibration standard to that interpolated from 400 and 100 kHz response.

To verify the process consider the following example using a data set for ⅞ inch diameter tubing having inspection frequencies 400, 200 and 100 kHz. The data from 400 and 100 kHz will be used to interpolate the 200 kHz data. In this case the 200 Hz data was used to calculate C and the resulting interpolation compared directly to the actual data. FIG. 2 shows the response of various simulations associated with the calibration tube both interpolated and measured. The difference in the two responses is minimal. More specifically FIG. 2 shows a Comparison of a 200 kHz response of the calibration standard to that interpolated from 400 and 100 kHz. The left image shows the responses of the tube support simulation and 100% discontinuity while the right image shows the responses of the 60%, 40% and 20% discontinuities. The lower images show the 200 kHz responses, and the upper images show the interpolated responses. The extent of the discontinuity is determined by the phase. For example, the left discontinuity reflected signal is deeper than the right reflected signal.

Figure 3:
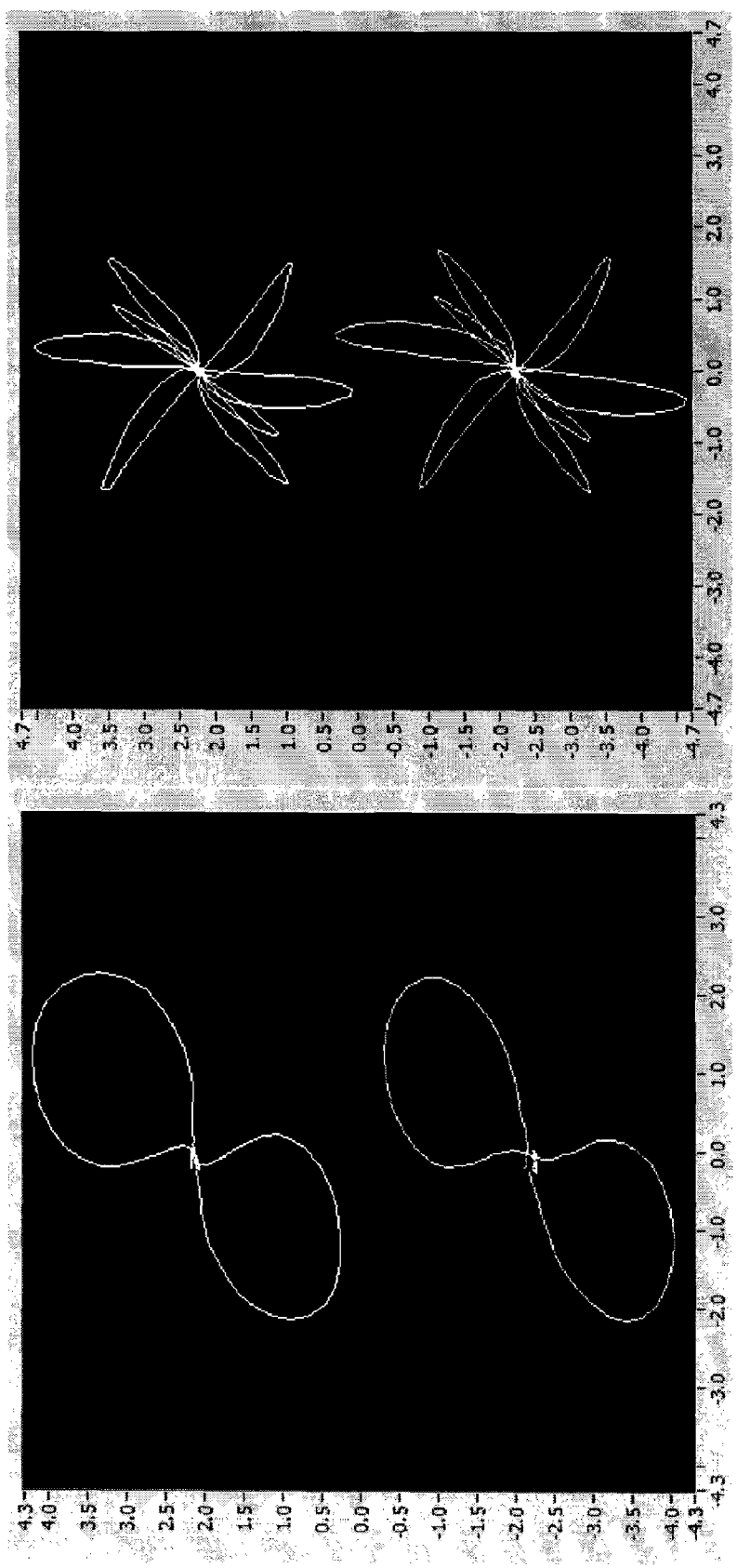
FIG. 3 is a computer screen image showing a comparison of a 380 kHz response of the calibration standard to that interpolated from 760 and 130 kHz response.

As another example the C matrix calculated for the 7/8 inch diameter tubing was applied to the data collected for a 5/8 inch diameter tube. Since the wall thickness is less for the small diameter tube the inspection frequencies are adjusted to compensate resulting in the use of 760, 380 and 130 kHz. FIG. 3 shows a comparison of the interpolated 380 kHz response with that measured. The lower images are the measured responses, and the upper images are the interpolated responses. Again the differences in the responses are minimal. More specifically FIG. 3 shows a Comparison of a 380 kHz response of the calibration standard to that interpolated from 760 and 130 kHz using the coefficient calculated for use with the 7/8 inch diameter tube. The left image shows the responses of the tube support simulation while the right image shows the responses of the 100%, 60%, 40% and 20% discontinuities.

Figure 4:
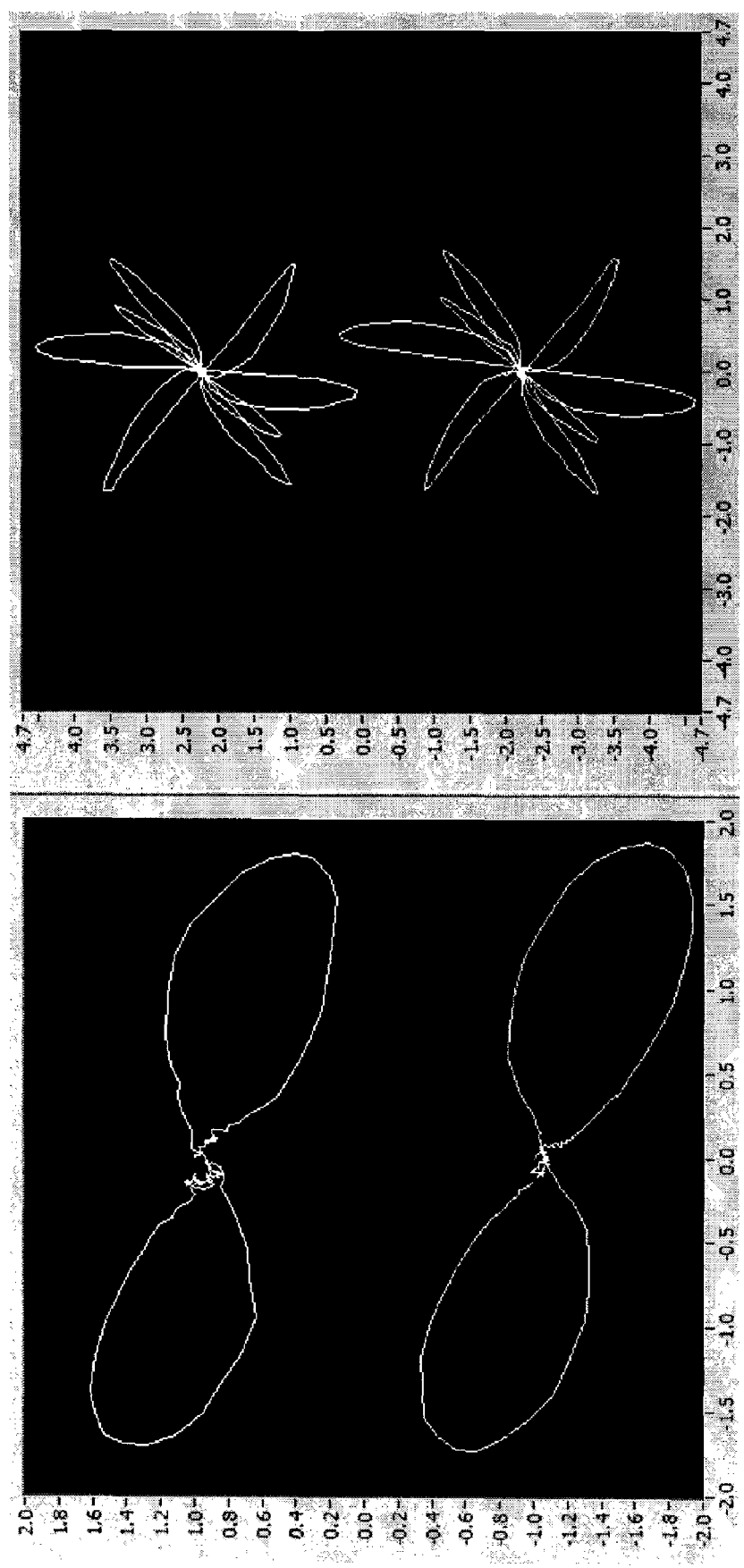
FIG. 4 is a computer screen image of a comparison of 760 kHz response of the calibration standard to that extrapolated from 380 and 130 kHz response.

An additional functionality for which the process is applicable is to extrapolate the response to a frequency range outside of that bounded by the examination frequencies. In this scenario $f_b$ could be either greater than $f_1$ or less than $f_3$ in the above examples. As an example of this capability, the 5/8 inch diameter tubing data were used. In this case the inspection data obtained at 380 and 130 kHz was used to extrapolate the response for 760 kHz. FIG. 4 shows a comparison of the extrapolated 760 kHz response with that measured. The lower images are the measured responses, and the upper images are the extrapolated responses. Again the differences in the responses are minimal. More specifically FIG. 4 shows a Comparison of a 760 kHz response of the calibration standard to that extrapolated from 380 and 130 kHz. The left image shows the responses of the tube support simulation while the right image shows the responses of the 100%, 60%, 40% and 20% discontinuities.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention, which is to be given the full breadth of the appended claims and any and all equivalence thereof.

What is claimed is:

1. A method of interpolating or extrapolating eddy current inspection data at a desired frequency, comprising the steps of:

acquiring a first set of eddy current inspection data as a result of a first scan by a first eddy current probe operated at a first frequency;

acquiring a second set of eddy current inspection data as a result of a second scan by a second eddy current probe operated at a second frequency;

acquiring a reference set of eddy current inspection data from a third scan of a reference probe operated at the first frequency, the second frequency and the desired frequency; and inferring the eddy current inspection data at the desired frequency based upon the first set, the second set and the reference set of eddy current inspection data.

2. The method of claim 1 wherein the desired frequency is either the first frequency or the second frequency.

3. The method of claim 1 wherein the steps of acquiring the first set of eddy current inspection data, acquiring the second set of eddy current inspection data and acquiring the reference set of eddy current inspection data are acquired with the same type of probe and under substantially similar inspection conditions.

4. The method of claim 1 including the step of rotating and scaling either the first set of eddy current inspection data or the second set of eddy current so that the only difference from a comparison perspective between the first set of eddy current inspection data and the second set of eddy current inspection data is the first frequency that the first probe was operated at and the second frequency that the second probe was operated at.

5. The method of claim 4 including the step of rotating and scaling the reference set of eddy current inspection data to match a scale and orientation of the first set of eddy current inspection data and the second set of eddy current inspection data.

6. The method of claim 1 wherein the reference set of eddy current inspection data includes a number of responses to different discontinuities and structures.

7. The method of claim 6 including the step of obtaining the reference set of eddy current inspection data from an eddy current probe scan of a calibration tube.

8. The method of claim 1 wherein at least one of either the first set of eddy current inspection data, the second set of eddy current inspection data or the reference set of eddy current inspection data is acquired using a mathematical model.

9. The method of claim 1 wherein the desired frequency is the second frequency and the inferring step converts the first set of eddy current inspection data to the second frequency using the formula:

$$C*(A)=(B)$$

Where A is the first set of eddy current inspection data and B is the second set of eddy current inspection data and C is a calculated matrix of coefficients.

10. The method of claim 9 wherein C is constructed from a subset of the reference set of eddy current inspection data.

11. The method of claim 10 wherein once matrix C is calculated it can be utilized to interpolate inspection frequencies for any data set that has been obtained in a fashion similar to the reference set of eddy current inspection data.

12. The method of claim 11 wherein the matrix C can be used to interpolate inspection data for different tubing diameters.

* * * * *